United States Patent [19]

Popovich et al.

[11] 4,239,041
[45] Dec. 16, 1980

[54] METHOD FOR CONTINUOUS AMBULATORY PERITONEAL DIALYSIS

[76] Inventors: Robert P. Popovich, 2928 Kassarine Pass, Austin, Tex. 78704; Jack W. Moncrief, 3633 West Lake, Austin, Tex. 78746

[21] Appl. No.: 931,098

[22] Filed: Aug. 4, 1978

Related U.S. Application Data

[62] Division of Ser. No. 773,912, Mar. 3, 1977, abandoned.

[51] Int. Cl.³ ............................................. A61M 5/00
[52] U.S. Cl. ................................................. 128/213 A
[58] Field of Search ........... 128/213 A, 214 R, 214 B, 128/227, 230; 210/321, 22

[56] References Cited

U.S. PATENT DOCUMENTS

| | | | |
|---|---|---|---|
| 3,157,201 | 11/1964 | Littman | 128/214 B X |
| 3,545,438 | 12/1970 | DeVries | 128/213 A |
| 3,626,938 | 12/1971 | Versaci | 128/214 B |
| 3,730,183 | 5/1973 | Goldsmith et al. | 128/213 A |
| 3,872,863 | 3/1975 | Lasker et al. | 128 A/213 A |

OTHER PUBLICATIONS

Grollman et al., AMA Archives of Internal Med. 1951, pp. 379–390.
Boen et al., Trans. Amer. Soc. Artific Inter. Orgs., vol. VIII, 1962, pp. 256–262.

*Primary Examiner*—Dalton L. Truluck
*Attorney, Agent, or Firm*—Arnold, White & Durkee

[57] ABSTRACT

A process for the removal of toxins from the body in a continuous manner while the patient is totally ambulatory. The process involves the infusion of a dialysate fluid under prescribed conditions into the peritoneal cavity. The toxic solutes are transported across the peritoneum membrane into the dialysate fluid by the natural processes of diffusion and convection. The dialysate fluid and the toxins are then removed after a prescribed residence phase. Apparatus includes an indwelling balloon catheter surgically implanted within the peritoneal cavity of a patient, a dacron cuff surgically attached to the abdominal wall, and an external quick connect coupling attached to the catheter. Apparatus may also include a wearable microbiological filter unit for reducing the risk of peritonitis during infusion of dialysate fluid.

10 Claims, 2 Drawing Figures

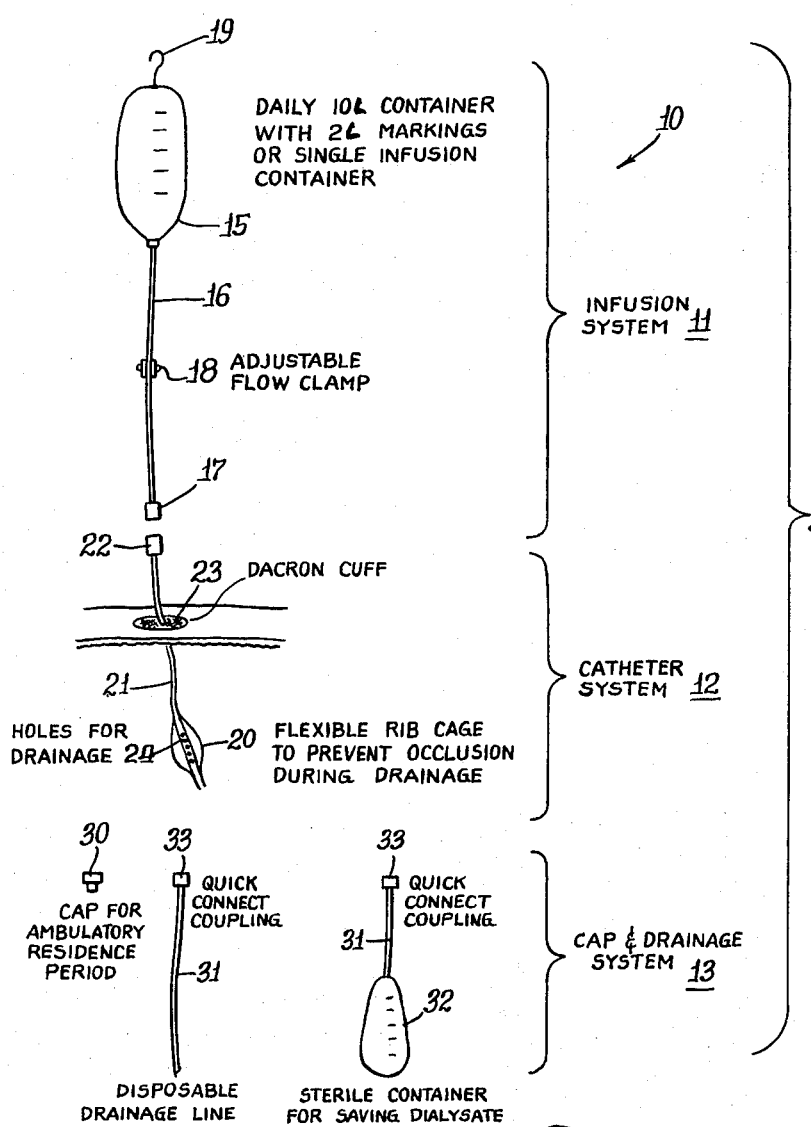
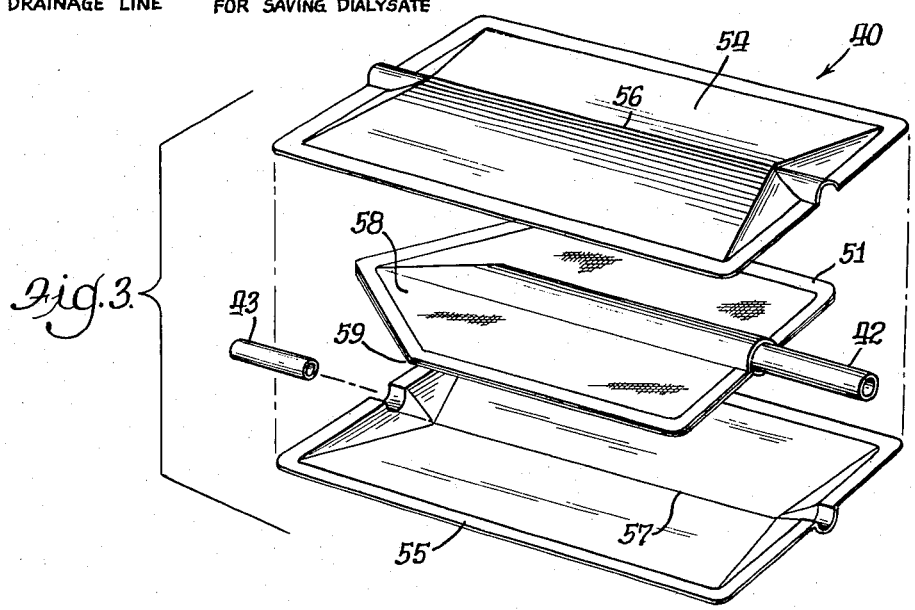

METHOD FOR CONTINUOUS AMBULATORY PERITONEAL DIALYSIS

This is a division of application Ser. No. 773,912, filed Mar. 3, 1977, now abandoned.

BACKGROUND OF THE INVENTION

1. Field of the Invention

The invention relates generally to the field of Surgery, and more particularly to fluid infusion methods and devices for performing peritoneal dialysis within a patient.

2. Description of the Prior Art

Several of the functions performed by human kidneys are the removal of waste metabolites, the maintenance of fluid, electrolyte and acid-base balances, and hormone and enzyme syntheses[1]. Loss of normal kidney function (acute or chronic renal insufficiency) is generally treated through dialysis therapy or transplantation. Transplantation, if successful, restores all the normal functions. Dialysis partially replaces some of the normal kidney functions. For example, it does not replace the hormone or enzyme functions, among others, as evidenced by the greatly reduced blood hemoglobin levels in chronic uremic patients.

Two types of dialysis thereapy are generally employed. Hemodialysis is most commonly used in which the blood is cleansed by passage through an artificial kidney in an extracorporeal membrane system. The waste metabolites diffuse across the membrane and are removed by a washing dialysate solution. Excess fluid is removed by pressure-induced ultrafiltration. The other approach is termed peritoneal dialysis, in which the dialysate solution is infused directly into the abdominal cavity. This cavity is lined by the peritoneal membrane which is highly vascularized. Metabolites are removed by diffusion from the blood to the dialysate across the peritoneal membrane. Excess fluid is removed by osmosis induced by a hypertonic dialysate solution.

Current dialysis treatments are generally performed intermittently under high efficiency conditions. The treatments are usually performed two or three times per week. The length of the treatment depends upon the desired reduction in blood waste metabolite levels, but usually averages 4-6 hours per hemodialysis and 24-48 hours for peritoneal dialysis. The time difference reflects the higher efficiency of hemodialysis, which is a primary reason for its greater popularity. Both procedures result in partial correction of abnormal metabolite, fluid, electrolyte and pH levels during the treatment. Blood metabolite levels are greatly reduced followed by a slow concentration buildup between dialyses. Kjellstrand[2] (1976) has hypothesized that the resulting concentration fluctuations may be detrimental to the patient's health. In fact, high efficiency hemodialyzers are not generally used to their full potential because of a characteristic disorder termed the "disequilibrium syndrome" which develops in certain patients. These patients develop headache, nausea, vomiting, and severe blood pressure alterations after two to three hours of dialysis. This condition often persists throughout the treatment leaving the patient weak and exhausted. It is hypothesized by Arieff[3], et al. (1975) that this syndrome is a result of large intracellular to extracellular concentration (and osmotic) gradients with concomitant fluid shifts, particularly across the "blood-brain barrier".

The Arieff hypothesis is supported by the results of Popovich[4], et al. (1975) who have investigated the consequences of physiological resistance on metabolite removal from the patient-artificial kidney system. Vitamin B-12 and insulin were selected as representative middle molecules in ther investigation. They have shown that very little of the larger test metabolites are cleared from the intracellular body pools during the dialysis treatment. This is caused by the high resistance to mass transfer across the cellular membranes and results in a large post dialysis concentration rebounds as the pools equilibrate in the interdialytic period.

The conventional hemodialysis procedures use an inordinately large amount of dialysate fluid, approximately 450 liters/week. It is contemplated that the procedure of the present invention will utilize approximately 70 liters/week.

SUMMARY OF THE INVENTION

The Continuous, Ambulatory Peritoneal Dialysis (CAPD) process of the present invention differs in several fundamental ways from all current conventional dialysis processes. It is totally different from the most popular process (hemodialysis) in that it employs a natural body membrane which obviates the need for an artificial kidney or for blood access.

The fact that CAPD is continuous results in stable, low blood toxic levels. Current peritoneal dialysis processes are intermittent (usually employed extensively two or three times per week). Such intermittent treatment results in wide toxin fluctuations at much higher levels than CAPD, which is detrimental to the patient's well-being.

As used herein, the term "continuous" means that a substantially constant presence of dialysate fluid is maintained within a patient at all times, except for that amount of time required to perform an exchange of fluid. The use of the term "continuous" in connection with the present invention is to be distinguished from the use and meaning of that term in connection with intermittent peritoneal dialysis procedures wherein a circulation loop is established through the peritoneal cavity.

The CAPD process obtains optimum use (100% efficiency) of dialysate fluid. Current processes employ short residence times with the intent of minimizing toxin levels in the dialysate to achieve the maximum toxin removal rate. These inefficient high removal rates are required because of the short intermittent nature of current processes.

The CAPD process is ambulatory—the patient being free to perform his normal daily duties while being treated. Patients undergoing conventional peritoneal dialysis processes are not ambulatory. They must remain by their dialysate supply (usually by machine) during the entire 24 to 48 hours of their treatment.

As used herein, the term "ambulatory" means that a patient receiving dialysis treatment is not constrained in his physical movement by attachment to a dialysis machine or to a dialysis supply that is in a fixed location.

The CAPD process is economical to use—no machines at all are requied. The contemplated usage of dialysate fluid is approximately 70 liters/week, compared with 450 liters/week for conventional hemodialysis.

The greatest advantage of all is the overall comfort and well-being of the patient using the CAPD.

BRIEF DESCRIPTION OF THE DRAWINGS

FIG. 1 is an exploded view of the components of the CAPD system of the present invention;

FIG. 3 is an exploded perspective view of a wearable microbiological filter unit designed for use as an auxiliary component in the system.

DETAILED DESCRIPTION OF THE PREFERRED EMBODIMENT

Figure 2:
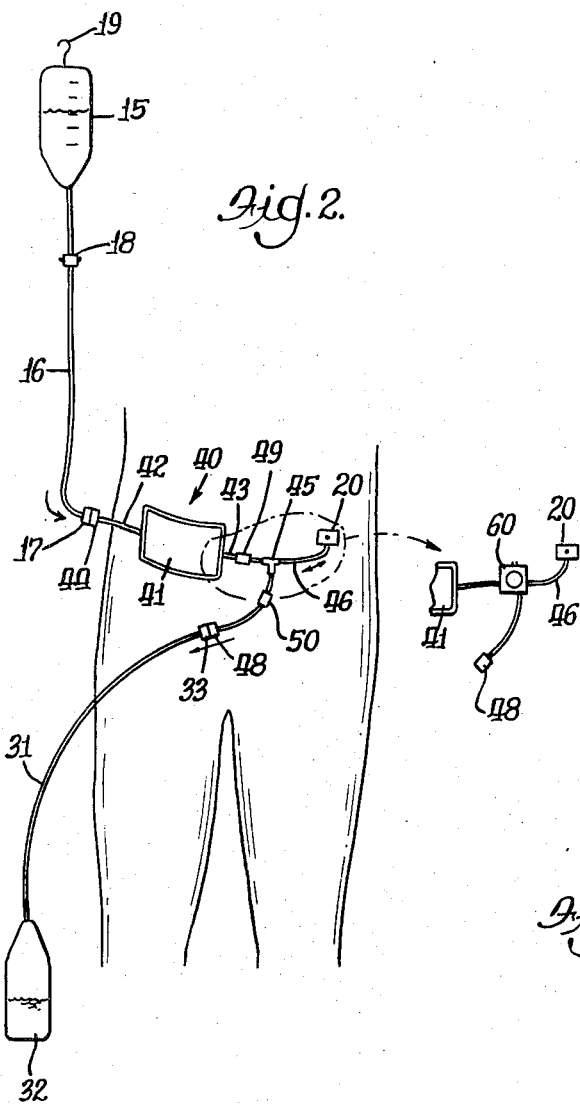
FIG. 2 is a schematic view of the invention as intended to be used on a patient.

The continuous, ambulatory peritoneal dialysis system of the present invention is illustrated in simplest form in FIG. 1 and is designated generally by the numeral 10. The overall system 10 comprises: an infusion system 11, a catheter system 12, and a cap and drainage system 13.

The infusion system 11 comprises a dialysate bottle or bag 15 having an outlet tube 16 which terminates at one-half of a quick connect coupling 17. An adjustable flow control clamp 18 is attached to the tube 16 for regulating the rate of fluid discharge from the bag 15. The bag 15 preferably has a volume capacity of 10 to 12 liters and has graduations at 2 liter intervals. The bag 15 may also have a hook 19 at its top for hanging it at some desired elevation above the attachment to a patient.

The catheter system 12 comprises a surgically implanted indwelling catheter 20 having a connecting tube 21 which terminates at a mating half of a quick connect coupling 22, and a dacron cuff 23 which is surgically implanted in the abdominal wall of a patient. The peritoneal catheter 20 may be, for example, a Goldberg Balloon type as supplied by the American Medical Products Corporation, or a Tenckhoff catheter. The catheter 20 is formed with a plurality of holes 24 and a flexible rib cage 25 adapted to prevent occlusion of the holes 24 during drainage. The dacron cuff 23 is adapted to allow tissue ingrowth and thereby provide an effective barrier to the entry of bacteria into the peritoneal cavity. The tube 21 extends through the dacron cuff 23 and provides external connection by means of the coupling 22.

The cap and drainage system 13 comprises an attachable cap 30 for mounting on the coupling 22 during the ambulatory residence period, a disposable drainage tube 31, and a sterile drainage container 32 for receiving used dialysate. The tube 31 carries a mating half of a quick connect coupling 33 for attachment to the coupling 22 during the drainage period.

In operation, the CAPD system 10 is utilized as follows:

Dialysate fluid is infused into a patient by attaching the coupling 17 to the coupling 22 and allowing approximately 2 liters to pass through the tube 16 to the catheter 20. The rate of flow of the fluid is controlled in a conventional manner by adjustment of the flow control clamp 18. The coupling 17 is then disconnected and the cap 30 placed on the coupling 22 for the ambulatory residence period which may last for approximately 4 to 5 hours. The cap 30 is then removed and the drain coupling 33 attached to the coupling 22. The spent dialysis fluid iss drained from the patient's peritoneal cavity by gravity through the tube 31 into the drainage container 32. The cycle just described is then repeated so as to maintain a substantially constant presence of the dialysate fluid within the patient and thereby provide for continuous dialysis.

A slightly modified embodiment of the invention is illustrated in FIG. 2 which shows the CAPD system as intended to be used on a patient. The system illustrated includes a wearable millipore filter unit 40 intended to minimize the introduction of bacteria into the peritoneal cavity during infusion of dialysate fluid. The filter unit 40 is interposed in the supply line 16 between the supply bottle 15 and the indwelling catheter 20. The filter unit 40 comprises a relatively flat filter body 41, a fluid inlet conduit 42, and an outlet tube or conduit 43. The inlet tube 42 has a quick connect coupling 44 adapted to be attached to the coupling 17. The outlet tube 43 is attached to one branch of a "T" connector 45. A second branch of the "T" connector is attached to a tube 46 leading to the catheter 20, and the third branch is connected to a tube 47 which leads to the drainage bottle 32. The tube 47 carries a quick connect coupling 48 adapted to be attached to the coupling 33 of the drain tube 31. Fluid cut-off clamps 49 and 50 are attached to the tubes 43 and 47, respectively. The clamps 49 and 50 are released alternately during infusion and drainage, respectively.

The wearable microbiological filter unit 40 is shown in exploded form in FIG. 3. The unit comprises the relatively flat and flexible body or housing 41, a central leaf-type filter 51, the inlet tube 42, and outlet tube 43. The outer shell or housing 41 preferably is made of two halves 54 and 55 cast from flexible, medical grade silicone elastomer bonded together into a shape that can conform to body curvature. The halves 54 and 55 also may be formed with raised longitudinal spines 56 and 57, respectively, adapted to prevent collapse of the outer shell against the filter 51. The filter 51 preferably is formed of two shells 58 and 59 of 0.22μ pore size membrane material bonded together at their edges. The inlet tube 42 and outlet tube 43 preferably are made of standard, commercially available silicone elastomer tubing.

Figure 4:
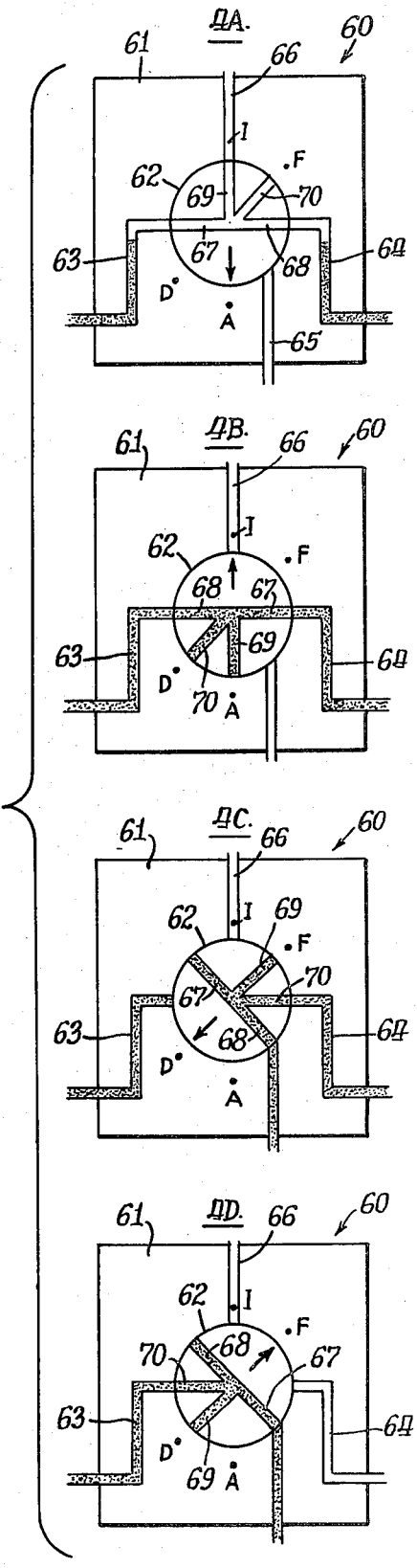
FIG. 4 is a fragmentary schematic view of an air bubble trap and flow directing valve also adapted for use in the system.

It is deemed desirable, if not imperative, to minimize the risk of introducing air into the peritoneal cavity during infusion of the dialysate fluid. To this end, a device such as the bubble trap and flow directing valve 60, illustrated schematically in FIG. 4, may also be included to advantage within the system 10. The valve structure 60 shown can supplement or substitute for the "T" connector 45 and clamps 49 and 50. The valve 60 comprises a relatively flat valve body 61, preferably made of clear plastic, and a rotatable valve core 62, also preferably made of clear plastic. The valve body 61 is formed with an inlet channel 63, an outlet channel 64, a drain channel 65, and an air bleed channel 66. The valve core 62 is formed with interconnected radial channels 67, 68, 69, and 70, as illustrated. The inlet channel 63 and outlet channel 64 are constructed so as to form an inverted "U" configuration. The inlet channel 63 is connected to the outlet tube 43 of the filter unit 40. (Alternatively, the entire valve structure 60 may be constructed as an integral part of the filter unit 40). The outlet channel 64 is connected to the catheter 20, and the drain channel 65 is adapted to be connected to the drainage bottle 32.

With the valve structure 60 oriented in a vertical plane, and with the valve core 62 turned to the "A" position, (as shown in FIG. 4A), any air trapped in the channels 63 and 64 can be bled through the air bleed channel 66 to atmosphere.

Once all the air has been bled from the line, the valve core 62 is turned to the "I" position (as shown in FIG. 4B) for infusion of dialysate fluids through channels 63, 68, 67, and 64 to the catheter 20. When the desired amount of fluid has been infused, the coupling 17–44 is disconnected and a cap placed on the coupling 44 for the period of residency. The coupling half 48 is also capped during the residency period.

After the desired period of residency within the peritoneal cavity, the spent dialysate fluid is drained by uncapping the coupling half 48, connecting the coupling 33 to 48, and turning the valve core 62 to the "D" position (as shown in FIG. 4C). In this position, the inlet channel 63 is cut off, and fluid is drained backwards through the outlet channel 64, through channels 70 and 68 to the drain channel 65. When drainage has been completed, the valve core 62 is returned to the "I" position, the drain bottle 32 disconnected, and the supply bottle 15 reconnected for infusion to the inlet tube 42. The cycle is then repeated as described above.

It is contemplated that the filter unit 40 and valve structure 60 may be flushed periodically with a formalin solution, or the like, to prevent the growth of bacteria within the filter and related conduits. To accomplish this, the valve core 62 is turned to the "F" position (as shown in FIG. 4D), and communication to the outlet channel 64 is cut off. The formalin solution is passed through the inlet tube 42, filter unit 40, through inlet channel 63, valve core channels 70 and 68 to the drain channel 65. The formalin solution is cleared by passing through a portion of dialysate fluid thereafter, before turning the valve core 62 to the "I" position for infusion.

MATHEMATICAL MODEL

The blood metabolite levels of patients are governed by a balance between the generation rate and the removal rate of the particular toxin in question. Theoretical relationships have been derived which predict the predialysis metabolite concentrations under discontinuous hemodialysis and peritoneal dialysis situations[5-7]. Similar expressions have been derived which predict the instantaneous blood and dialysate metabolite concentration levels during peritoneal dialysis infusions[8]. These analyses result in equations which are fairly complex for the general case. If steady state conditions can be assumed, the equations can be greatly simplified. Under these conditions, the steady state blood metabolite level $C_B$ is given by:

$$C_B = (G/K) \tag{1}$$

where G is the net generation rate and K is the total solute clearance (the sum of the dialysis clearance plus the residual renal clearance).

Alternatively, the net solute clearance necessary to maintain a prescribed blood metabolite level may also be computed. For example, equation (1) predicts that a total clearance of 7.1 ml/min is required assuming that a steady state blood urea nitrogen (BUN) concentration level of 70 mg/dl is desired with a BUN generation rate of 5.0 mg/min (15.4 g urea/day). This corresponds to a total clearance of approximately 10 liters per day.

This result is routinely employed by nephrologists. Patients are generally placed on some dialysis regimen when their residual renal clearance diminishes significantly below 7 ml/min.

The mathematical model also presents a simplification which is possible if the dialysate fluid totally equilibrates with the blood, i.e., $C_D = C_B$. For these conditions, the dialysance clearance equals the dialysate flow rate, $K_D = Q_D$, and equation (1) can be rewritten as:

$$C_B = \frac{G}{Q_D(1 + \frac{K_R}{Q_D})} \tag{2}$$

where $K_R$ = residual renal clearance. For the anuric case ($K_R = 0$) and equation (2) further simplified to:

$$C_B = (G/Q_D) \tag{3}$$

This analysis yields the hypothesis that a patient can be adequately dialyzed with acceptable BUN levels if only 10 liters of dialysate fluid per day are allowed to continuously equilibrate with body fluids (i.e. a dialysis clearance of 7.0 ml/min and a steady state BUN level of approximately 70 mg/dl).

CLINICAL TECHNIQUE

The desired equilibration of metabolite between blood and dialysate fluid can be readily accomplished with intermittent peritoneal dialysis utilizing the system 10 described above. Normal peritoneal dialysis procedure is to infuse 2 liters of dialysate with a residence time of 15 to 60 minutes[9]. I have discovered that if the residence time is extended to approximately 4½ hours, a patient can perform 5 exchanges per day with sufficient time for infusion and drainage. This long residence period has been found to be sufficient for equilibration between plasma and the dialysate for urea and creatinine. Five exchanges per day at two liters per exchange yields the 10 liters/day which has been hypothesized to be required to maintain the patient with acceptable BUN levels. Steady state may be assumed since five exchanges are performed each day with relatively long residence times which compares favorably with the usual three hemodialysis treatments per week. This equilibrium peritoneal dialysis technique is fundamental to the Continuous, Ambulatory Peritoneal Dialysis procedure of the invention described and claimed herein.

EXAMPLE

Equilibrium peritoneal dialysis according to the present invention was conducted on a 40-year old, 190 lb., 5'9" male over a five-month period through use of an indwelling Tenckhoff catheter. The patient had a history of surgical removal of his right kidney at an early age secondary to a traumatic injury. He had developed nephrotic syndrome approximately 18 months prior to reaching end stage renal disease. He had well established atherosclerotic coronary artery disease with angina pectoris. Cardiac catheterization and coronary arteriography revealed atherosclerotic changes of the left circumflex coronary artery and a 90% occlusion of small obtuse marginal branch on that side. The right coronary artery revealed stenosis 1 cm. long in the mid portion with approximately 50% obstruction. He was said to have had Buerger's disease at age 28 and had previously had a surgical procedure on the left iliac area at that age. A gastric mucosal biopsy demonstrated Menetrier's disease at age 39. He had hypercholestolemia and hypertriglyceridemia and had been diagnosed as having mild adult onset diabetes for approximately four years. Both his father and mother had diabetes, the mother requiring insulin. His glomerular filtration rate in September, 1974, was 14 ml/min, with a creatinine level of 9.9 mg/dl. He had 8 grams of protein in the urine per 24 hours at that time.

On eight separate occasions, efforts were made to establish a subcutaneous arteriovenous fistula, or the establishment of a Quintin-Schribner shunt. All of these attempts were unsuccessful because of thrombosis; only on one occasion was a fistual utilized for a single dialysis. It was recommended to the patient that he be transferred to a center where chronic peritoneal dialysis could be instituted. This patient was unwilling or unable to do. In view of these circumstances, the equilibrium-peritoneal dialysis technique defined herein was undertaken as a life-saving necessity.

After obtaining appropriate informed consent, the procedure of peritoneal dialysis using 5 two-liter exchanges per 24 hours was instituted. Infusion required 10 minutes, relying only on hydrostatic pressure, and was followed by an equilibration period averaging 260 minutes. Drainage of the dialysate averaged fifteen minutes. Three minutes were required for tubing connection yielding 288 minutes per exchange. The procedure was originally conducted with Dianeal®, 1.5% solution in the hospital. This did not allow for adequate water removal, so 4.25% solution was substituted on a variable schedule until it was determined that alternate 1.5% and 4.25% solutions could be used to remove approximately 2000 cc. of fluid per day in excess of that instilled into the peritoneum; the patient was uncooperative in maintaining fluid restrictions. The procedure was carried out on an experimental basis by the patient in the hospital for approximately one month. After stabilization of the patient on the new procedure, he was trained to conduct the procedure in his home. Within the first month at home he had an episode of peritonitis which subsequently resulted in obstruction of the chronic peritoneal catheter. The catheter was replaced and, subsequent to that, no obstructive problems developed.

The patient complained of intermittent abdominal pain which was felt to be related to the 4.25% hypertonic solution or to the pH of the solutions. The pH was adjusted with sodium bicarbonate, but he continued to exhibit intermittent abdominal pain. This did not, however, prevent him from carrying out normal physical activity, including making several trips to distant cities by carrying his dialysate solutions with him in the back of his car. The patient also complained of intermittent difficulty in sleeping because of abdominal distension.

The patient was oliguric during the course of the study. He had an estimated creatinine residual renal clearance of 5.0 ml/min and was anorexic with nausea and vomiting at the initiation of the study on June 30, 1975. His BUN was 70 mg/dl while under strict dietary protein restriction. Immediately after commencement of treatment in the hospital his diet restrictions were removed and his BUN's remained at 70 mg/dl with a significant increase in patient well-being. The BUN levels then diminished and stabilized in the 35 to 45 mg/dl range with creatinines in the 7 to 10 mg/dl range. The alleviation of the symtoms of chronic uremia in the patient was comparable to parients on hemodialysis. A creatinine residual clearance of 3.0 ml/min was measured on Oct. 10, 1975. The treatment was continued by the patient in his home until Dec. 9, 1975 at which time he was successfully transplanted with a cadaveric C-match kidney. He currently has a glomerular filtration rate of 96 ml/min.

CLINICAL EVALUATION

Clinical evaluation of the above example has been conducted and reported in the technical literature.[8] In order to quantify the treatment, the concentration levels of urea, creatinine, uric acid, glucose and tritium tagged cyancobalamin were followed on a single exchange on Nov. 14, 1975 and on a multi-day basis. The single exchange study was conducted by injecting a loading dose of 1000 µg of cyanocobalamin followed 24 hours later by the tagged cyancobalamin. After an additional 24-hour equilibration period, blood and dialysate samples were obtained at 30-minute intervals throughout the equilibration period.

Representative dialysate samples were obtained by mixing in situ via withdrawing and reinfusing, 50 ml of dialysate ten times immediately prior to aspiration of the sample. Concentration levels of the uremic toxins were determined by use of the Technicon SMA-12 analyzer, while cyanocobalamin levels were obtained via normal liquid scintillation counting techniques.

The dialysis clearances ($K_D$) of the various substances are normally determined from the average blood concentration ($\overline{C_B}$), residence time (t), drained dialysate volume ($V_D$) and concentration ($C_D$) by the expression:

$$K = \frac{C_D V_D}{\overline{C_B} t} \tag{4}$$

For the case of urea and creatinine, the blood and dialysate concentrations equilibrate, $C_D = C_B$, such that the equation (4) simplifies to:

$$K_D = \frac{V_D}{t} = Q_D \tag{5}$$

where $V_D$ is the drained dialysate volume (the sum of the infusion volume plus ultrafiltration volume).

The results for an average residence time of 288 minutes are presented in Table I below. The mean drained dialysate volume for the patient was 2,400 ml.

TABLE I

Equilibrium Peritoneal Dialysis Metabolite Clearances

| Compound | Mol. Wt. | K, ml/min |
| --- | --- | --- |
| Urea | 60 | 8.3 |
| Creatinine | 113 | 8.3 |
| Uric Acid | 168 | 7.7 |
| Cyanocobalamin | 1355 | 5.7 |

The experimental mean urea dialysis clearance of 8.3 ml/min is slightly greater than the required clearance value predicted in the development of the hypothesis. The increase is caused by the ultra filtered fluid.

The residual creatinine renal clearance was determined to be 3.0 ml three weeks prior to the quantative study. From this the total clearance, K, for urea and creatinine can be estimated to be:

$$K = K_D + K_R \tag{6}$$
$$K = 8.3 + 3.0$$
$$K = 11.3 \text{ ml/min.}$$

Equation (1) above can be employed to calculate predicted steady state concentrations of urea and creatinine from this value and the generation rate, G. The results plus the experimental values are presented in Table II.

TABLE II

Predicted and Experimental Metabolite Levels

| Solute | G, mg/min | K, ml/min | $C_B$, predicted, mg% | $C_B$, experimental, mg% |
|---|---|---|---|---|
| Urea | 5.0 | 11.3 | 44 | 35–45 |
| Creatinine | 1.4 | 11.3 | 12 | 7–10 |

The predicted values are in good agreement with the experimental results. It appears that the actual generation rates for the patient was less than those assumed for the general patient population. This is in line with the diabetic diet of the patient and the restricted activity resulting from his cardiovascular complications.

Middle molecule clearances as defined by Vitamin B-12 with this procedure are at acceptable levels. In fact, the steady state middle molecule metabolite concentration levels of patients with this technique will be considerably less than those undergoing hemodialysis. For example, 18 hours/week of hemodialysis at a B-12 clearance of 25 ml/min yields a total clearance-time product of 27 liters/week. The corresponding equilibrium peritoneal dialysis clearance of 5.7 ml/min (neglecting residual renal clearance) for 168 hours/week yields a total clearance-time product of 57 liters/week. This predicts that the middle molecule concentration level for patients utilizing the new procedure will be less than one-half of that of patients on hemodialysis. This primarily caused by the increased time factor, i.e., equilibrium peritoneal dialysis is conducted 24 hours/day. The steady state character of the treatment will also allow for continuous equilibration across the cellular membrane which will circumvent the limitations imposed by inner body resistances which have been reported for discontinuous hemodialysis techniques.[4]

In summary, the CAPD system of the present invention offers a number of significant advantages over existing dialysis techniques. The fact that toxic solutes are removed continuously eliminates the discomfort associated with body adjustment to the wide fluctuation in chemical imbalances that occur before and after conventional dialysis.

The CAPD process results in low blood toxic metabolite levels which can be prescribed within limits by an attending physician by adjusting the dialysate volume infused.

The CAPD process results in lower blood levels of larger toxic solutes (so-called "middle molecules") because of its continuous nature.

The CAPD process does not require blood access as with all conventional hemodialysis processes which constitute approximately 90% of current dialysis practice. The administration of an anticoagulant (heparin) is not required. There is no blood loss in equipment, or contact of blood on foreign surfaces as is true with all hemodialysis processes.

The CAPD system does not require an artificial kidney or the use of complicated equipment which must be purchased and maintained.

The CAPD system is wearable and the patient is free to go about his normal activities while the dialysis is being performed.

The embodiments of the invention shown and described are by way of example only, and it is to be understood that many changes and modifications might be made thereto without departing from the spirit of the invention. The invention is not to be construed as limited to the embodiments shown and described, except in-so-far as the claims may be so limited.

BIBLIOGRAPHY

1. Abbrecht P. H., "An Outline Renal Structure and Function", CEP Symp. Series, 64, 1 (1968).
2. Kjellstrand, C. M., "Future Directions for the Ak-CUP Program", Proceedings Contractors Conference, Artificial Kidney Chronic Uremia Program, NIH, HEW 9, (1976).
3. Arieff, A. I, Guisado, R., Massry, S. G., "Uremic Encephalopathy: Studies on Biochemical Alterations in the Brain", Kidney Intern., 7, S-194 (1975).
4. Popovich, R. P., Hlavinka, D. J., Bomar, J. B., Moncrief, J. W., and Dechers, J. F., "The Consequences of Physiological Resistances on Metabolite Removal from the Patient-Artificial Kidney System", Trans. Amer. Soc. Artif. Int. Organs, 21, 108 (1975).
5. Popovich, R. P., Moncrief, J. W., "The prediction of metobolite accumulation concomitant with renal insufficiency; the middle molecule anomaly". Trans. Amer. Soc. Artif. Organs, 20:377 (1974).
6. Bomar, J. B., Decherd, J. F., Hlavinka, D. J., Moncrief, J. W., and Popovich, R. P., "The elucidation of maximum efficiency-minimum cost peritoneal dialysis protocols." Trans. Amer. Soc. Artif. Int. Organs, 20:120 (1974).
7. Sargent, J. A. and Gotch, F. A., "The analysis of concentration dependence of uremic lesions in clinical studies." Kidney International 1 (S-2):35 (1975).
8. Popovich, R. P. and Pyle, W. K., "Preliminary Verification of the low dialysis clearance hypothesis via a novel equilibrium peritoneal dialysis technique." Sec. Australasian Conf. on Heat and Mass Transfer (1977).
9. Maxwell, M. W., Rockney, R. E., Kleeman, C. R., and Twiss, M. R., "Peritoneal Dialysis I: Technique and Applications", J. Amer. Med. Assoc., 180: 917 (1959).

I claim:

1. A method of continuous, ambulatory peritoneal dialysis, which comprises the step of establishing a substantially constant presence of dialysate fluid within the peritoneum of a patient at all times over an extended period of time using apparatus comprising:
   an in-dwelling catheter adapted to be surgically implanted in the peritoneal cavity of a patient and having a supply tube for extending through the abdominal wall of the patient; and
   a bag adapted to be interconnected with the supply tube and carried by the patient during dialysis for dispensing dialysate fluid through the supply tube to the peritoneal cavity of the patient and for receiving spent dialysate drained from the peritoneal cavity of the patient.

2. The method of claim 1 using apparatus which further comprises:
   a quick disconnect coupling attached to the end of the supply tube; and
   a coupling attachment on the bag for interconnection with the coupling on the end of the supply tube.

3. The method of claim 1 using apparatus which further comprises:
   a coupling attached to the end of the supply tube; and
   a cap for attachment to the coupling on the end of the supply tube to seal the end thereof.

4. The method of claim 8 using apparatus which further comprises a wearable microbiological filter interposed between the catheter and the bag for preventing the introduction of bacteria to the peritoneum.

5. A method for continuous ambulatory peritoneal dialysis of a patient, the patient being unattached to automatic cycling dialysis apparatus, comprising the steps of:
- infusing dialysate fluid into the patient's peritoneal cavity;
- allowing the dialysate fluid to remain within the patient's pertioneal cavity for a residence period time during which the patient remains ambulatory and unattached to a dialysis fluid supply that is in a fixed location;
- draining the dialysate fluid from the patient's peritoneal cavity after the time period; and
- immediately repeating the aforesaid steps, the steps being repeated several times per day, every day, at intervals corresponding to the residence time period, so as to maintain a substantially constant presence of dialysate fluid within the patient at all times.

6. The method of claim 5 wherein the residence time period is at least four hours and the aforesaid steps are repeated at least three times in each twenty-four hour period.

7. A method for continuous ambulatory peritoneal dialysis of a patient unattached to automatic cycling dialysis apparatus, as maintenance treatment for chronic end-stage renal disease, comprising the steps of:
- infusing dialysate fluid into the patient's peritoneal cavity;
- allowing the dialysate fluid to remain in the patient's peritoneal cavity for a dwell time during which the patient is ambulatory and unattached to a dialysis fluid supply that is in a fixed location;
- exchanging fresh dialysate fluid for spent dialysate fluid after the residence period of time by draining the spent dialysate fluid from the patient's peritoneal cavity and immediately infusing fresh dialysate fluid into the patient's peritoneal cavity;
- repeating the exchange of dialysate fluid several times per day at intervals corresponding to the residence period of time such that a substantially constant presence of dialysis fluid is maintained and dialysis is occurring essentially continuous for twenty-four hours per day, every day, except for drainage and infusion times.

8. The method of claim 7, wherein the mean dwell time is at least four hours.

9. A method for continuous ambulatory peritoneal dialysis of a patient, the patient being unattached to automatic cycling dialysis apparatus, as maintenance treatment for chronic end-stage renal disease to reduce uremic toxicity, and in which nitrogen waste product removal and production are balanced at a low level of plasma urea concentration, comprising the steps of:
- infusing dialysate fluid into the patient's peritoneal cavity;
- exchanging the dialysate fluid after a mean dwell time period during which the patient is ambulatory and remains unattached to a dialysis fluid supply that is in a fixed location;
- repeating the step of exchanging dialysate fluid several times per day to maintain a substantially constant presence of dialysate fluid, so that dialysis is occurring essentially twenty-four hours per day, every day, except for drainage and infusion times, and is continuous.

10. A method for continuous ambulatory peritoneal dialysis of a patient, the patient being unattached to automatic cycling dialysis apparatus and having an implanted catheter that leads to the peritoneal cavity, comprising the steps of:
- attaching to the catheter a small plastic bag containing about two liters of dialysate fluid;
- infusing the contents of the bag into the patient's peritoneal cavity;
- allowing the dialysate fluid to remain in the patient's peritoneal cavity for a mean dwell time of at least four hours, during which time the patient is ambulatory and remains unattached to a dialysis fluid supply that is in a fixed location;
- draining the dialysate fluid from the patient's peritoneal cavity and disconnecting the plastic bag from the catheter; and
- repeating the aforesaid steps at least three times per day, every day, at intervals of at least four hours to maintain a substantially constant presence of dialysate fluid in the patient's peritoneal cavity, so that dialysis is occurring essentially twenty-four hours per day, every day, except for drainage and infusion times, and is continuous.

* * * * *